US005750361A

United States Patent [19]

Prusiner et al.

[11] Patent Number: 5,750,361

[45] Date of Patent: May 12, 1998

[54] FORMATION AND USE OF PRION PROTEIN (PRP) COMPLEXES

[75] Inventors: Stanley B. Prusiner; Kiyotoshi Kaneko; Fred E. Cohen, all of San Francisco, Calif.

[73] Assignee: The Regents of the University of California, Oakland, Calif.

[21] Appl. No.: 556,823

[22] Filed: Nov. 2, 1995

[51] Int. Cl.$^6$ .......................... C12Q 1/37; G01N 31/00; G01N 21/00; G01N 1/22

[52] U.S. Cl. .................................. 435/23; 435/24; 435/6; 435/188; 435/325; 436/2; 436/164; 436/181; 530/350; 536/23.1

[58] Field of Search .......................... 530/350; 536/23.1; 435/23, 24, 6, 188, 240.2; 436/2, 164, 181

[56] References Cited

U.S. PATENT DOCUMENTS 5,565,186 10/1996 Prusiner et al. .

OTHER PUBLICATIONS

Barry, R., et al., Monoclonal Antibodies to the Cellular and Scrapie Prion Proteins, *The Journal of Infectious Diseases*, vol. 154, No. 3, pp. 518–521, (Sep. 1986).

Chandler, R.L., et al., Encephalopathy in Mice Produced by Inoculation with Scrapie Brain Material, *The Lancet*, 1:1378–1379, (Jun. 24, 1961).

Chien, C., et al., The two–hybrid system: A method to identify and clone genes for proteins that interact with a protein of interest, Proc. Natl. Acad. Sci. USA, 88:9578–9582, (Nov. 1991).

Fradkin, J., et al., Creutzfeldt–jakob Disease in Pituitary Growth Hormone Recipients in the United States, *JAMA*, 265, No. 7, 880–884.

Gajdusek, D.C., et al., Experimental Transmission of a Kuru–like Syndrome to Chimpanzees, *Nature*, 209:794–796.

Gabizon, R., et al., Immunoaffinity purification and neutralization of scrapie prion infectivity, *Proc. Natl. Acad. Sci. USA*, 85:6617–6621, (Sep. 1988).

Gassett, M., et al., Predicted α–helical regions of the prion protein when synthesized as peptides form amyloid, *Proc. natl. Acad. Sci. USA*, 89:10940–10944 (Nov. 1992).

Gibbs, C.J., et al., Creutzfeldt–Jakob Disease (Spongiform Encephalopathy): Transmission to the Chimpanzee, *Science*, 161:388–389 (Jul. 1968).

Hadlow, W.J., et al., Scrapie and Kuru, *The Lancet*, 2:289–290, (Sep. 5, 1959).

Harries–Jones, R., et al., Creutzfeld–Jakob disease in England and Wales, 1980–1984: a case–control study of potential risk factors, *Journal of Neurology, Neurosurgery, and Psychiatry*, 51:1113–1119, (1988).

Kascsak, R., et al., Mouse Polyclonal and Monoclonal Antibody to Scrapie–Associated Fibril Proteins, *Journal of Virology*, vol. 61, No. 12, 3688–3693, (Dec. 1987).

Kocisko, David, A., et al., Cell–free formation of protease–resistant prion protein, *Nature*, 370:471–474, (Aug. 1994).

Marsh, R.F., et al., Comparison of Scrapie and Transmissible Mink Encephalopathy in Hamsters. II. Clinical Signs, Pathology, and Pathogenesis, *The Journal of Infectious Diseases*, vol. 131, No. 2, 104–110, (Feb. 1975).

Nguyen, J., et al., Prion Protein Peptides Induce α–Helix to β–Sheet Conformational Transitions, *Biochemistry*, 34:4186–4192, (1995).

Pan, K., et al., Conversion of α–helices in β–sheets features in the formation of the scrapie prion proteins, *Proc. Natl. Acad. Sci. USA*, 90:10962–10966, (Dec. 1993).

Prusiner, S.B., et al., Attempts to restore scrapie prion infectivity after exposure to protein denaturants, *Proc. Natl. Aca. Sci. USA*, 90:2793–2797, (Apr. 1993).

Prusiner, S.B., et al., Scrapie Prions Aggregate to Form Amyloid–like Birefringent Rods, *Cell*, 35:349–358, (Dec. 1983).

Rogers, M., et al., Epitope Mapping of the Syrian Hamster Prion Protein Utilizing Chimeric and Mutant Genes in a Vaccinia Virus Expression System, *The Journal of Immunology*, 147, No. 10, 3568–3574, (Nov. 1991).

Scott, M., et al., Transgenic Mice Expressing Hamster Prion Protein Produce Species–Specific Scrapie Infectivity and Amyloid Plaques, *Cell*, 59:847–857, (Dec. 1989).

Stahl, N., et al., Structural Studies of the Scrapie Prion Protein Using Mass Spectrometry and Amino Acid Sequencing, *Biochemistry*, 32:1991–2002, (1993).

Telling, G.C., et al., Prion Propagation in Mice Expressing Human and Chimeric PrP Transgenes Implicates the Interaction of Cellular PrP with Another Protein, *Cell*, 83:79–90, (Oct. 1995).

Turk, E., et al., Purification and properties of the cellular and scrapie hamster prion proteins, *J. Eur. Biochem.*, 176:21–30, (1988).

Zhang H., et al., Conformational Transitions in Peptides Containing Two Putative α–Helices of the Prion Protein, *J. Mol. Biol.*, 250:514–526, (1995).

Pan et al., "Conversion of Alpha–Helices into Beta–Sheets Features in the Formation of the Scrapie Prion Proteins," Proceedings of the National Academy of Science, USA., vol. 90, Dec., 1993, pp. 10962–10966.

Kretzschmar et al., "Molecular Cloning of a Human Prion Protein cDNA," DNA, vol. 5, No. 4, 1986, pp. 315–324.

Caughey et al., "Scrapie–Associated PrP Accumulation and its Inhibition: Revisiting the Amyloid–Glycosaminoglycan Connection," Annals of Trhe New York Academy of Sciences, vol. 724, Jun. 6, 1994, pp. 290–294.

*Primary Examiner*—Paula K. Hutzell
*Assistant Examiner*—Mark Navarro
*Attorney, Agent, or Firm*—Karl Bozicevic; Bozicevic & Reed LLP

[57] ABSTRACT

Prion protein (PrP) peptides having at least one α-helical domain and forming a random coil conformation in aqueous solutions bind cellular PrP ($PrP^C$) to form a complex having characteristics of the scrapie isoform ($PrP^{Sc}$). Methods for screening compounds able to inhibit or decrease the binding of PrP peptides to $PrP^C$ are disclosed, as well as methods for assaying $PrP^{Sc}$.

27 Claims, 1 Drawing Sheet

Syrian Hamster (SHa) and Human (Hu) 90-231 $PrP^C$ Sequence

```
      90        100        110        120        130        140        150
SHa:  G QGGGTHNQWN KPSKPKTNMK HMAGAAAAGA VVGGLGGYML GSAMSRPMMH FGNDWEDRYY
Hu:   G QGGGTHSQWN KPSKPKTNMK HMAGAAAAGA VVGGLGGYML GSAMSRPIIH FGSDYEDRYY

                160        170        180        190        200        210
SHa:    RENMNRYPNQ VYYRPVDQYN NQNNFVHDCV NITIKQHTVT TTTKGENFTE TDIKIMERVV
Hu:     RENMHRYPNQ VYYRPMDEYS NQNNFVHDCV NITIKQHTVT TTTKGENFTE TDVKMMERVV

                220        230 231
SHa:    EQMCTTQYQK ESQAYYDGRR S
Hu:     EQMCITQYER ESQAYYQRGS S
```

FIG. 1

FORMATION AND USE OF PRION PROTEIN (PRP) COMPLEXES

GOVERNMENT RIGHTS

The United States Government may have certain rights in this application pursuant to Grant Nos. AG10770, AG08967, NS07219, NS14069, NS22786 and AG021732, awarded by the National Institutes of Health.

FIELD OF THE INVENTION

This invention relates to assays for testing drugs by using natural and synthetic prion protein peptides.

BACKGROUND OF THE INVENTION

Prions are infectious pathogens that cause central nervous system spongiform encephalopathies in humans and animals. Prions are distinct from bacteria, viruses and viroids. The predominant hypothesis at present is that no nucleic acid component is necessary for infectivity of prion protein. Further, a prion which infects one species of animal (e.g., a human) will not infect another (e.g., a mouse).

A major step in the study of prions and the diseases that they cause was the discovery and purification of a protein designated prion protein ("PrP") (Bolton et al. (1982) Science 218:1309–11; Prusiner et al. (1982) Biochemistry 21:6942–50; McKinley et al. (1983) Cell 35:57–62). Complete prion protein-encoding genes have since been cloned, sequenced and expressed in transgenic animals. $PrP^C$ is encoded by a single-copy host gene (Basler et al. (1986) Cell 46:417–28) and is normally found at the outer surface of neurons. Prion diseases are accompanied by the conversion of PrPC into a modified form called $PrP^{Sc}$. However, the actual biological or physiological function of PrPc is not known.

The scrapie isoform of the prion protein ($PrP^{Sc}$) is necessary for both the transmission and pathogenesis of the transmissible neurodegenerative diseases of animals and humans. See Prusiner (1991) Science 252:1515–1522). The most common prion diseases of animals are scrapie of sheep and goats and bovine spongiform encephalopathy (BSE) of cattle (Wilesmith & Wells (1991) Microbiol. Immunol. 172:21–38). Four prion diseases of humans have been identified:

(1) kuru,
(2) Creutzfeldt-Jakob Disease (CJD),
(3) Gerstmann-Sträussler-Scheinker Disease (GSS), and
(4) fatal familial insomnia (FFI) (Gajdusek (1977) Science 197:943–960; Medori et al. (1992) N. Engl. J. Med. 326:444–449). The presentation of human prion diseases as sporadic, genetic and infectious illnesses initially posed a conundrum which has been explained by the cellular genetic origin of PrP.

Most CJD cases are sporadic, but about 10–15% are inherited as autosomal dominant disorders that are caused by mutations in the human PrP gene (Hsiao et al. (1990) Neurology 40:1820–1827; Goldfarb et al. (1992) Science 258:806–808; Kitamoto et al. (1994) Proc. R. Soc. Lond. (In press). Iatrogenic CJD has been caused by human growth hormone derived from cadaveric pituitaries as well as dura mater grafts (Brown et al. (1992) Lancet 340:24–27). Despite numerous attempts to link CJD to an infectious source such as the consumption of scrapie infected sheep meat, none has been identified to date (Harries-Jones et al. (1988) J. Neurol. Neurosurg. Psychiatry 51:1113–1119) except in cases of iatrogenically induced disease. On the other hand, kuru, which for many decades devastated the Fore and neighboring tribes of the New Guinea highlands, is believed to have been spread by infection during ritualistic cannibalism (Alpers (1979) *Slow Transmissible Diseases of the Nervous System*, Vol. 1, S. B. Prusiner and W. J. Hadlow, eds. (New York: Academic Press), pp. 66–90).

The initial transmission of CJD to experimental primates has a rich history beginning with William Hadlow's recognition of the similarity between kuru and scrapie. In 1959, Hadlow suggested that extracts prepared from patients dying of kuru be inoculated into non-human primates and that the animals be observed for disease that was predicted to occur after a prolonged incubation period (Hadlow (1959) Lancet 2:289–290). Seven years later, Gajdusek, Gibbs and Alpers demonstrated the transmissibility of kuru to chimpanzees after incubation periods ranging from 18 to 21 months (Gajdusek et al. (1966) Nature 209:794–796). The similarity of the neuropathology of kuru with that of CJD (Klatzo et al. (1959) Lab Invest. 8:799–847) prompted similar experiments with chimpanzees and transmissions of disease were reported in 1968 (Gibbs et al. (1968) Science 161:388–389). Over the last 25 years, about 300 cases of CJD, kuru and GSS have been transmitted to a variety of apes and monkeys.

The expense, scarcity and often perceived inhumanity of such experiments have restricted this work and thus limited the accumulation of knowledge. While the most reliable transmission data has been said to emanate from studies using non-human primates, some cases of human prion disease have been transmitted to rodents but apparently with less regularity (Gibbs et al. (1979) *Slow Transmissible Diseases of the Nervous System*, Vol. 2, S. B. Prusiner and W. J. Hadlow, eds. (New York: Academic Press), pp. 87–110; Tateishi et al. (1992) *Prion Diseases of Humans and Animals*, Prusiner, et al., eds. (London: Ellis Horwood), pp. 129–134).

The infrequent transmission of human prion disease to rodents has been cited as an example of the "species barrier" first described by Pattison in his studies of passaging the scrapie agent between sheep and rodents (Pattison (1965) *NINDB Monograph* 2, D. C. Gajdusek, C. J. Gibbs Jr. and M. P. Alpers, eds. (Washington, D.C.: U.S. Government Printing), pp. 249–257). In those investigations, the initial passage of prions from one species to another was associated with a prolonged incubation time with only a few animals developing illness. Subsequent passage in the same species was characterized by all the animals becoming ill after greatly shortened incubation times.

The molecular basis for the species barrier between Syrian hamster (SHa) and mouse was shown to reside in the sequence of the PrP gene using transgenic (Tg) mice (Scott et al. (1989) Cell 59:847–857). SHaPrP differs from MoPrP at 16 positions out of 254 amino acid residues (Basler et al. (1986) Cell 46:417–428; Locht et al. (1986) Proc. Natl. Acad. Sci. USA 83:6372–6376). Tg(SHaPrP) mice expressing SHaPrP had abbreviated incubation times when inoculated with SHa prions. When similar studies were performed with mice expressing the human, or ovine PrP transgenes, the species barrier was not abrogated, i.e., the percentage of animals which became infected were unacceptably low and the incubation times were unacceptably long. Thus, it has not been possible, for example in the case of human prions, to use transgenic animals (such as mice containing a PrP gene of another species) to reliably test a sample to determine if that sample is infected with prions. The seriousness of the health risk resulting from the lack of such a test is exemplified below.

More than 45 young adults previously treated with HGH derived from human pituitaries have developed CJD (Koch et al. (1985) N. Engl. J. Med. 313:731–733; Brown et al. (1992) Lancet 340:24–27; Fradkin et al. (1991) JAMA 265:880–884; Buchanan et al. (1991) Br. Med. J. 302:824–828). Fortunately, recombinant HGH is now used, although the seemingly remote possibility has been raised that increased expression of wild-type $PrP^c$ stimulated by high HGH might induce prion disease (Lasmezas et al. (1993) Biochem. Biophys. Res. Commun. 196:1163–1169). That the HGH prepared from pituitaries was contaminated with prions is supported by the transmission of prion disease to a monkey 66 months after inoculation with a suspect lot of HGH (Gibbs et al. (1993) N. Engl. J. Med. 328:358–359). The long incubation times associated with prion diseases will not reveal the full extent of iatrogenic CJD for decades in thousands of people treated with HGH worldwide. Iatrogenic CJD also appears to have developed in four infertile women treated with contaminated human pituitary-derived gonadotrophin hormone (Healy et al. (1993) Br. J. Med. 307:517–518; Cochius et al. (1993) Aust. N.Z. J. Med. 20:592–593; Cochius et al. (1992) J. Neurol. Neurosurg. Psychiatry 55:1094–1095) as well as at least 11 patients receiving dura mater grafts (Nisbet et al. (1989) J. Am. Med. Assoc. 261:1118; Thadani et al. (1988) J. Neurosurg. 69:766–769; Willison et al. (1991) J. Neurosurg. Psychiatric 54:940; Brown et al. (1992) Lancet 340:24–27).

Recently, two doctors in France were charged with involuntary manslaughter of a child who had been treated with growth hormones extracted from corpses. The child developed Creutzfeldt-Jakob Disease. (See *New Scientist*, Jul. 31, 1993, page 4). According to the Pasteur Institute, since 1989 there have been 24 reported cases of CJD in young people who were treated with human growth hormone between 1983 and mid-1985. Fifteen of these children have died. It now appears as though hundreds of children in France have been treated with growth hormone extracted from dead bodies at the risk of developing CJD (see *New Scientist*, Nov. 20, 1993, page 10).

These cases underscore the urgent need to develop therapies for PrPSc-mediated disease such as CJD. Although many lines of evidence support the idea that $PrP^C$ is converted into the modified scrapie isoform $PrP^{Sc}$, the conditions under which this occurs is not known. Knowledge of the conditions under which scrapie infectivity is generated de novo would be useful in the development of assays to identify compounds able to inhibit the generation of $PrP^{Sc}$. Compounds able to inhibit the in vitro conversion of $PrP^C$ to $PrP^{Sc}$ could be useful for the treatment and prevention of prion-mediated diseases in animal and human subjects at risk.

Despite progress made in identifying prions, PrP genes and the like, there does not exist any assay which would be useful in assaying compounds in the treatments of diseases caused by prions. In view of the serious nature of diseases caused by prions, there exists a need for such an assay as provided by the present invention.

SUMMARY OF THE INVENTION

The present invention provides assay methods using naturally occurring and synthetic prion protein peptides (PrP peptides) which induce a conformational change in $PrP^C$ by formation of a prion protein complex exhibiting the hallmarks of the isoform $PrP^{Sc}$, e.g., a $PrP^{Sc}$-like complex. This assay is useful for screening compounds able to prevent the in vitro induction of $PrP^C$ to the $PrP^{Sc}$-like complex. Compounds identified by the method of the invention are candidates for the development of therapies for the treatment of $PrP^{Sc}$-mediated diseases, e.g., compounds able to inhibit or slow the development of $PrP^{Sc}$-mediated diseases in a subject at risk for development of a $PrP^{Sc}$-mediated disease.

Accordingly, the invention features PrP peptides able to bind $PrP^C$ or a PrP variant, forming a prion protein complex having one or more $PrP^{Sc}$-like characteristics of an increased β-sheet content, diminished aqueous solubility, and/or resistance to proteolytic digestion relative to $PrP^C$. The PrP peptides of the invention are characterized as having at least one a-helical domain and/or forming a random coil conformation in an aqueous solution. The PrP peptides of the invention include naturally occurring, recombinant and synthetic peptides. Preferred peptides include random coil peptides having amino acid sequence of residues 90–145 (SEQ ID NO:1) of the naturally occurring PrP protein amino acid sequence (FIG. 1) and residues 90–231 (SEQ ID NO:2) of the naturally occurring $PrP^C$ protein. The 90–145 amino acid portion of the naturally occurring amino acid sequence includes two α-helical domains. The 90–231 amino acid sequence includes four α-helical domains.

The invention includes PrP peptides having minor modifications of amino acids 90–145 (SEQ ID NO:1) or 90–231 (SEQ ID NO:2), which may result in enhanced binding to $PrP^C$ and/or enhanced induction of a $PrP^{Sc}$-like complex. In a preferred embodiment, the PrP peptide has the 90–145 amino acid sequence in which alanine at position 117 is replaced with valine (PrP peptide 90–145(A117V). The invention further includes peptides containing deletions of one or more amino acids which result in the modification of the structure of the resultant molecule without significantly altering its ability to bind $PrP^C$ to form a prion protein complex or to induce a conformational change in $PrP^C$ to form a $PrP^{Sc}$-like complex.

The prion protein complex formed by binding of PrP peptides to $PrP^C$ or a PrP variant is characterized by an increased β-sheet content, diminished solubility, and/or increased resistance to proteolytic digestion relative to $PrP^C$. The prion protein complex is a $PrP^{Sc}$-like complex which forms fibrous aggregates, sediments at 100,000×g for 1 h, exhibits resistance to proteolytic digestion and displays a high β-sheet content. The prion protein complex preferably contains a 20–100% increased β-sheet content relative to $PrP^C$; and more preferably, the prion protein complex has an increased β-sheet content of about 50–100% relative to $PrP^C$. The insoluble prion protein complex is at least about 20% protease resistant, preferably about 45–100% protease resistant, and more preferably, about 60–100% protease resistant.

In one aspect, the invention features an assay method for screening compounds able to decrease or inhibit the binding of a PrP peptide to $PrP^C$ or a PrP variant. A test compound is contacted with a first component $PrP^C$ or PrP variant in the presence of a second component PrP peptide, and the ability of the test compound to prevent the formation of a prion protein complex determined. The first component $PrP^C$ may be the synthetic, naturally derived, or recombinant protein from any species source of interest, including human, mouse, hamster, bovine, or ovine. Preferably, $PrP^C$ is the human prion protein, and more preferably, $PrP^C$ is a recombinantly produced human prion protein. First component $PrP^C$ also includes variants of the naturally occurring or recombinant protein. In one embodiment, the first component is the recombinant peptide having amino acid residues 90–231 of human $PrP^C$ (SEQ ID NO:10).

In a related aspect, the invention features a method for screening compounds able to decrease or inhibit the induction of a prion protein complex between a first component $PrP^C$ and a second component PrP peptide. A test compound is contacted with $PrP^C$ in the presence of a PrP peptide, and determined on of a prion protein complex determined.

A test compound able to prevent or decrease PrP peptide binding to $PrP^C$ and/or prevent or decrease induction of a prion protein complex may be useful in vivo for preventing or treating a $PrP^{Sc}$-mediated disease, such as Creutzfeldt-Jacob Disease (CJD), Gerstmann-Sträussler-Scheinker Disease (GSS), fatal familiar insomnia (FFI), kuru, scrapies, bovine spongiform encephalopathy (BSE), and any other disease connected to formation of $PrP^{Sc}$. A test compound identified by the method of the invention as able to inhibit or decrease the in vitro induction of a prion protein complex can be tested in an in vivo model of $PrP^{Sc}$ disease for ability to prevent development of a $PrP^{Sc}$disease.

In another aspect, the invention features an assay for $PrP^{Sc}$. The presence of $PrP^{Sc}$ in a sample is determined from the displacement of a PrP peptide from the prion protein complex. In one embodiment, a prion protein complex is allowed to form between a labelled PrP peptide and $PrP^C$, and a test sample added. The amount of displaced peptide is determined by measuring the amount of label in the supernatant fraction after centrifugation to pellet the insoluble prion protein complexes. In another embodiment, the first component $PrP^C$ is affinity labeled and immobilized after prion protein complex formation with a second component labelled PrP peptide. A test sample is added, and the amount of displaced labelled peptide is determined in the unbound phase.

In another aspect, the invention features a method for designing $PrP^C$ transgenes with improved ability to induce prion protein complex formation. Modified $PrP^C$ molecules are generated and their ability to form prion protein complexes determined as described above. By this method, modified transgenes with improved $PrP^{Sc}$ binding can be identified for use in improved prion bioassays. Such bioassays can be optimized for each species, e.g., human, bovine, ovine or porcine prions.

An important feature of the invention is that the methodology makes it possible to identify candidate compounds which prevent the in vitro induction of a $PrP^{Sc}$-like complex from the $PrP^C$ isoform.

An advantage of the invention is that methodology makes it possible to test candidate compounds so identified in existing in vivo models of $PrP^{Sc}$ diseases. Another advantage is in providing a rapid and convenient assay for $PrP^{Sc}$.

These and other objects, advantages, and features of the invention will become apparent to those persons skilled in the art upon reading the details of the methods, assays, and peptides of the invention as more fully described below.

BRIEF DESCRIPTION OF THE FIGURE

FIG. 1 is the amino acid sequence for Syrian hamster $PrP^C$ sequences 90–231 (SEQ ID NO:2) with specific differences to human $PrP^C$ 90–231 sequence (SEQ ID NO:10).

DETAILED DESCRIPTION

Before the present methods and controls are described, it is to be understood that this invention is not limited to particular methods, assays, or peptides described, as such methods, assays and peptides may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Definitions

The term "prion" shall mean an infectious particle known to cause diseases (spongiform encephalopathies) in humans and animals. "Prion" is a contraction of the words "protein" and "infection" and the particles are comprised largely if not exclusively of $PrP^{Sc}$ molecules encoded by a PrP gene. Prions are distinct from bacteria, viruses and viroids. Known prions include those which infect animals to cause scrapie, a transmissible, degenerative disease of the nervous system of sheep and goats as well as bovine spongiform encephalopathies (BSE) or mad cow disease and feline spongiform encephalopathies of cats. Four prion diseases known to affect humans are (1) kuru, (2) Creutzfeldt-Jakob Disease (CJD), (3) Gerstmann-Sträussler-Scheinker Disease (GSS), and (4) fatal familial insomnia (FFI). As used herein prion includes all forms of prions causing all or any of these diseases or others in any animals used—and in particular in humans and in domesticated farm animals.

There are a number of known variants to the human PrP gene. Further, there are known polymorphisms in the human, sheep and bovine PrP genes. The following is a list of such variants:

| Pathogenic Human Mutations | Human Polymorphisms | Sheep Polymorphisms | Bovine Polymorphisms |
|---|---|---|---|
| 2 octarepeat insert | Codon 129 Met/Val | Codon 171 Arg/Glu | 5 or 6 octarepeats |
| 4 octarepeat insert | Codon 219 Gly/Lys | Codon 136 Ala/Val | |
| 6 octarepeat insert | | | |
| 7 octarepeat insert | | | |
| 8 octarepeat insert | | | |
| 9 octarepeat insert | | | |
| Codon 102 Pro-Leu | | | |
| Codon 105 Pro-Leu | | | |
| Codon 117 Ala-Val | | | |
| Codon 145 Stop | | | |
| Codon 178 Asp-Asn | | | |
| Codon 180 Val-Ile | | | |
| Codon 198 Phe-Ser | | | |
| Codon 200 Glu-Lys | | | |
| Codon 210 Val-Ile | | | |
| Codon 217 Asn-Arg | | | |
| Codon 232 Met-Ala | | | |

As used herein, the term "PrP peptide" is broadly defined as any peptide which when contacted with naturally occurring or recombinant $PrP^C$ or PrP variant results in the induction of a conformational change which can be identified by presence of enhanced β-sheet formation, increased insolubility, and/or increased protease resistance relative to $PrP^C$, e.g., having $PrP^{Sc}$ characteristics. In one embodiment, PrP peptide shall mean a naturally occurring, recombinant, or synthetic amino acid sequence having a sequence substantially similar (e.g., 90% or greater homology) to a portion of the naturally occurring prion protein sequence having residues 90–145 (SEQ ID NO:1), or a portion thereof, and able to bind $PrP^C$ such that a prion protein complex is formed having one or more of the characteristics of $PrP^{Sc}$. In a second embodiment, PrP peptide shall mean a naturally occurring, recombinant, or synthetic amino acid sequence having a sequence substantially similar to a portion of the naturally occurring prion protein sequence having residues 90–231 (SEQ ID NO:10), or a portion thereof, and able to bind $PrP^C$ such that a $PrP^{Sc}$-like complex is formed. The PrP peptide is characterized as having at least one a-helical domain and/or having a random coil conformation in a aqueous solution. Further, the PrP peptide may be characterized as having a conformation in aqueous solution which is substantially devoid of β-sheet conformation. The conformation of a PrP peptide of the invention is determined by a number of methods known in the art, including circular dichroism (CD).

In specific embodiments, a PrP peptide of the invention is characterized as having between 1–4 α-helical domains and binding $PrP^C$ to form a prion protein complex. In preferred embodiment, the PrP peptide has the amino acid sequence of SEQ ID NO:1 or SEQ ID NO:10. The PrP peptide may have modifications of the amino acid sequence of SEQ ID NO:1 or SEQ ID NO:10, e.g., one or more amino acid changes, one or more amino acid deletions, and/or one or more amino acid insertions, so long as it retains the characteristics of having at least one α-helical domain and/or a random coil conformation in an aqueous solution, and binding $PrP^C$ to form a prion protein complex. Preferably, the changes, deletions, insertions, and the like, are in the sequence between amino acids 90–145. For example, PrP peptide 90–145 (A117V) contains the pathogenic mutation at amino acid residue 117 (alanine to valine) which causes the telencephalic and ataxic forms of GSS disease.

The terms "$PrP^{Sc}$-like complex", "prion protein complex", or "$PrP^C$/PrP peptide complex" are used interchangeably to mean a complex formed between $PrP^C$ and a PrP peptide which exhibits the hallmarks of the $PrP^{Sc}$ isoform characterized by formation of an insoluble pellet when centrifuged at 100,000×g for 1 h, and/or having a high β-sheet content typical of $PrP^{Sc}$, and/or exhibiting resistant to proteolytic digestion. The prion protein complex is formed between first and second components. A first component of the complex, $PrP^C$, may be a naturally occurring or recombinant PrP protein, or variant thereof. For example, in one specific embodiment, the first component $PrP^C$ is the naturally occurring $PrP^C$. In another specific embodiment, the first component PrPCis a N-terminus truncated $PrP^C$ protein having 90–231 amino acids (SEQ ID NO:10). The second component of the complex is a recombinant or synthetic PrP peptide. To form a $PrP^{Sc}$-like or prion protein complex, an excess of the second component, which has a random coil or α-helical conformation, is required. In specific embodiments, the second component PrP peptide has an amino acid sequence selected from one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease.

More specifically, "treatment" is intended to mean providing a therapeutically detectable and beneficial effect on a patient suffering from a PrP-related disease.

$PrP^{Sc}$ Formation

The formation of $PrP^{Sc}$ is a post-translational process (Borschelt et al. (1990) J. Cell Biol. 110:743–752) in which $PrP^C$ forms a complex with $PrP^{Sc}$ and is transformed into a second molecule of $PrP^{Sc}$ (Prusiner et al. (1990) Cell 63:673–686). While attempts to detect a covalent change that distinguishes $PrP^C$ from $PrP^{Sc}$ have been unsuccessful (Stahl et al. (1993) Biochemistry 32:1991–2002), spectroscopic studies demonstrated that $PrP^C$ contains ~40% α-helix and is devoid of β-sheet (Pan et al. (1993) Proc. Natl. Acad. Sci. USA 90:10962–10966). In contrast, $PrP^{Sc}$ has a high β-sheet content which correlates with scrapie infectivity (Prusiner et al. (1983) Cell 35:349–358; Caughey et al. (1991) Biochemistry 30:7672–7680; Gasset et al. (1993) Proc. Natl. Acad. Sci. USA 90:1–5; Safar et al. (1993) J. Biol. Chem. 268:20276–20284).

Studies of mice expressing Syrian hamster (SHa) PrP transgenes suggest that $PrP^C$ and $PrP^{Sc}$ form a complex during the formation of nascent $PrP^{Sc}$ (Prusiner et al. (1990) Cell 63:673–686). The present inventors were unable to demonstrate $PrP^{Sc}$ production through formation of such complexes by mixing purified fractions equimolar amounts of the two isoforms (Raeber et al. (1992) J. Virol. 66:6155–6163). Other investigators have demonstrated an interaction between $PrP^{Sc}$ and $PrP^C$ by mixing a 50-fold excess of $PrP^{Sc}$ with labeled $PrP^C$ (Kocisko et al. (1994) Nature 370:471–474).

Synthetic PrP peptides corresponding to regions of putative secondary structure and displaying conformational pluralism have been studied (Gasset et al. (1992) Proc. Natl. Acad. Sci. USA 89:10940–10944; Nguyen et al. (1995) Biochemistry 34:4186–4192). Transgenic studies with chimeric PrP genes suggest that $PrP^C$ and $PrP^{Sc}$ may interact within a central domain delimited by codons 96 and 169 (Scott et al. (1992) Protein Sci. 1:986–997; Scott et al. (1993) Cell 73:979–988; Telling et al. (1994) Proc. Natl. Acad. Sci. USA 91:9936–9940). The present disclosure presents the first physical evidence that PrP peptides encompassing the first two putative α-helical regions and mimicking many structural features of the two PrP isoforms, when mixed with $PrP^C$, induce formation of a complex which is resistant to proteolytic digestion and which sediments at 100,000×g for 1 h.

Previous work from this laboratory has shown that small PrP peptides can interact with each other to induce conformational changes (Nguyen et al. (1995) Biochemistry 34:4186–4192), and that a 56-residue peptide, SHa 90–145, corresponding to the N-terminus of PrP 27–30, displays multiple conformations (Zhang et al. (1995) J. Mol. Biol. 250:514–526). Example 2 below describes experiments elucidating the role of conformational form in the formation of a $PrP^{Sc}$-like complex. Labeled SHa$PrP^C$ was incubated with random coil or β-sheet forms of the PrP peptides SHa 90–145, SHa 109–122 and Mo 90–145, and their effect on induction of protease resistance determined. Mixtures of $PrP^C$ and SHa 90–145 formed fibrous aggregates which displayed the high β-sheet content typical of $PrP^{Sc}$.

Unexpectedly, it was found that random coil SHa 90–145 induced protease resistance, while SHa 90–145 in the β-sheet form did not. Mo 90–145 in either the random coil or β-sheet form did not induce protease resistance when incubated with SHaPr$P^C$.

In some experiments, *E. coli* expressed recombinant SHa 90–231 was used in place of Pr$P^C$. The mixture of SHa 90–145 and SHa 90–231 under the same conditions which generated the Pr$P^{Sc}$-like complex between Pr$P^C$ and SHa 90–145 resulted in formation of an insoluble complex exhibiting protease resistance.

To localize the region in which PrP peptides interact with Pr$P^C$, shorter peptides were examined, including the recombinant SHa 90–231 peptide. Neither H1 (containing residues 109–122) nor a longer version composed of residues 104–122 (104H1) induced protease resistance in Pr$P^C$. In aqueous buffers, H1 rapidly folds into β-sheets and polymerizes (Gasset et al. (1992) Proc. Natl. Acad. Sci. USA 89:10940–10944), while 104H1 is random coil (Nguyen et al. (1995) supra). Both SHa 109–141 and SHa 90–145 induced protease resistance. When the pathogenic A117V mutation causing both the telencephalic and ataxic forms of Gerstmann-Sträussler-Scheinker (GSS) disease (Dohura et al. (1989) Biochem. Biophys. Res. Commun. 163:974–979; Hsiao et al. (1991) Neurology 41:681–684; Mastrianni et al. (1995) Neurology (In Press)) was substituted in the peptide, ~65% of the radiolabeled Pr$P^C$ formed sedimentable complexes. Compared with the wild-type peptide, only 30–40% of the mutant SHa 90–145(A117V) peptide was needed to produce equivalent amounts of protease-resistant Pr$P^C$. When SHa 90–145 was substituted by SHa 90–231, an insoluble complex resulted which exhibited enhanced protease resistance.

The addition of 2% (w/v) Sarkosyl disrupted the prion protein complexes and rendered the Pr$P^C$ sensitive to protease activity. With SHa 90–145(A117V), about 30% of the [$^{35}$S-]- Pr$P^C$/PrP peptide complex exhibited protease resistance; whereas with SHa 90–145, only 10–15% was resistant.

Since the protease resistance of the Pr$P^C$/PrP peptide complexes resembled that of PrPSe (Turk et al. (1988) Eur. J. Biochem. 176:21–30; Meyer et al. (1986) Proc. Natl. Acad. Sci. USA 83:2310–2314; McKinley et al. (1991) J. Virol. 65:1440–1449) the physical properties of the Pr$P^C$/SHa 90–145 complex was investigated by FTIR spectra analysis, CD, and electron microscopy, of SHa 90–145 and the Pr$P^C$/SHa 90–145 complex (Example 3). Less than 10% of the [$^{35}$S-]Pr$P^C$ sedimented when SHaPr$P^C$ was incubated alone, whereas ~65% of the radiolabel pelleted with the addition of SHa 90–145(A117V). The sedimented Pr$P^C$/SHa 90–145 complex showed a substantial increase in β-sheet content compared to pelleted Pr$P^C$.

Anti-PrP monoclonal antibodies 3F4 and 13A5 bind to SHaPr$P^C$ within the region spanned by the SHa 90–145 peptide. 3F4 recognizes residues 109–112 (Rogers et al. (1991) J. Immunol. 147:3568–3574), and 13A5 recognizes residues 138–141 (Barry & Prusiner (1986) J. Infect. Dis. 154:518–521). The ability of these antibodies to prevent acquisition of protease resistance was examined (Example 4). Both mAbs were found to prevent the formation of protease-resistance Pr$P^C$/SHa 90–145 complexes.

Experiments were conducted to determine if Pr$P^C$ could spontaneously become protease resistant in the absence of PrP peptides (Example 5). In the absence of SHa 90–145 (A117V) approximately 1% of the Pr$P^C$ was found to be protease resistant, whereas about 30% of the prPC became resistant with the peptide. Experiments were conducted to determine if Pr$P^{Sc}$ mixed with Pr$P^C$ might render Pr$P^C$ protease resistant. Other investigators have reported that Pr$P^{Sc}$denatured in 3M Gdn-HCl undergoes renaturation and renders Pr$P^C$ resistant to proteolysis within 2 min of mixing (Kocisko et al. (1994) Nature 370:417–474). Since numerous attempts to renature prion infectivity from both Gdn and urea had failed (Prusiner et al. (1993) Proc. Natl. Acad. Sci. USA 90:2793–2797), the effect of 3M Gdn-HCl on Pr$P^{Sc}$ was investigated (Example 6). Mixing denatured Pr$P^{Sc}$ with Pr$P^C$ did not result in formation of protease-resistant Pr$P^C$.

It is estimated that 10–15% of Pr$P^C$ mixed with non-denatured Pr$P^{Sc}$ acquired protease resistance after 48 h (Example 6), in contrast to mixing with the SHa 90–145 (A117V) peptide where about 30% Pr$P^C$ demonstrated protease resistance (Example 5). After incubation with SHa 90–145 for 1 hr, about 35% of the [$^{35}$S-]Pr$P^C$ that exhibited protease resistance at 48 h was present, by 24 h, about 75% of the Pr$P^C$ was protease resistant. Experiments were unable to reproduce the report that protease-resistant [$^{35}$S-]Pr$P^C$ was generated within 2 min after mixing with a 50-fold excess of unlabeled Pr$P^{Sc}$ (Kocisko et al. (1994) Nature 370:471–474).

The interaction between Pr$P^C$ and Pr$P^{Sc}$ was found to be inhibited by anti-PrP mAb 3F4, but not by 13A5 (Example 7). The possibility that this difference between the two mAbs might indicate a critical role for the PrP residues in the vicinity of the 3F4 epitope, which is the N-terminus of the Hi region, was investigated by examining binding of a Pr$P^C$ truncated at the N-terminus and lacking the 3F4 epitope (Pr$P^C$-II). PrPC-II did not exhibit protease resistance after exposure to Pr$P^{Sc}$, supporting the notion that the Hi region, in which the 3F4 epitope lies, is particularly significant in Pr$P^C$-Pr$P^{Sc}$ binding (Pan et al. (1992) Protein Sci. 1:1343–1352; Haraguchi et al. (1989) Arch. Biochem. Biophys. 274:1–13).

Species and detergent effect on Pr$P^{Sc}$ binding to Pr$P^C$ were investigated (Example 8). When Mo 90–145 was mixed with SHaPr$P^C$, relatively little protease-resistant Pr$P^C$ was formed, and the addition of Sarkosyl rendered the complex sensitive to proteolysis. In contrast, the [$^{35}$S]Pr$P^C$/SHaPr$P^{Sc}$ complex was resistant to proteolysis, even when exposed to up to 2% Sarkosyl for 48 h before digestion. These results are consistent with the finding that SHa 90–145 mixed with SHaPr$P^C$ produced protease-resistant protein, whereas Mo 90–145 mixed with SHaPr$P^C$ did not.

Additional attempts to disrupt the Pr$P^C$/Pr$P^{Sc}$complexes under conditions likely to preserve the scrapie prion infectivity utilized detergents such as NP-40, Tween-10, Zwittergent 3–12, and sodium deoxycholate, alone or in combination with phospholipids to form detergent-lipid-protein complexes (Gabizon et al. (1988) Proc. Natl. Acad. Sci. USA 85:6617–6621). The possibility of disrupting these complexes using the anti-PrP 3F4 mAb and synthetic peptides containing residues 109–122 or 90–145 was investigated. Although the mAb and peptides were added to the complexes in molar ratios of 1000:1, they were unable to dissociate the [$^{35}$S-]Pr$P^C$ from Pr$P^{Sc}$. Addition of a 10-fold excess of cold PrP from CHO cells also failed to displace the [$^{35}$S-]Pr$P^C$ from the complex.

These findings provide evidence that Pr$P^C$ interacts through a domain which contains the first two putative α-helices and that a random coil configuration is required for interaction.

Assays

Screening for compounds which inhibit prion protein complex formation.

In one aspect, the present invention provides novel assays useful in identifying inhibitors of the formation of a $PrP^{Sc}$-like complex resulting from PrP peptide binding to $PrP^{C}$.

Although in vitro assays of the present invention can be configured in a number of ways, in a preferred configuration, a test compound is contacted with $PrP^{C}$, a PrP peptide is added to the test-compound/$PrP^{C}$ mixture, and the formation of a prion protein complex detected. Detection of a prion protein complex may be accomplished in a number of ways, including by formation of an insoluble complex, e.g., formation of a fibrous aggregate, of which at least 65% sediments at 100,000×g for 1 h at 20° C., and which is at least 20% protease resistant and exhibits substantial β-sheet conformation. Percent sedimentation, protease resistance, and conformation are determined by methods known in the art, such as those methods described below. Formation of a $PrP^{Sc}$-like complex in the presence of a test compound is compared to complex formation in the absence of the test compound (control). Preferably, a test compound will inhibit 20% or more complex formation relative to the control, more preferably, it will inhibit complex formation by 50% or more, and most preferably, by 75% or more.

As described above, an *E. coli* expressed PrP peptide, for example, SHa or Hu 90–231 (FIG. 1), may be used in place of naturally occurring $PrP^{C}$, or in place of a synthetic peptide. The advantages of the *E. coli* produced recombinant PrP proteins include the ability to generate high levels of PrP; the ability to change the sequence and length of PrP by site-directed mutagenesis of the PrP gene; absence of most post-translational modifications such as glycosylation; and ability to easily purify PrP from contaminants.

A compound identified by the assay method of the invention as inhibiting complex formation can be tested in an animal model of a $PrP^{Sc}$-mediated disease, and its ability to inhibit $PrP^{Sc}$ induction in vivo or treat a $PrP^{Sc}$-mediated disease determined. Such an animal model is described in co-pending U.S. patent application Ser. No. 08/449,485. As defined above, treatment of a $PrP^{Sc}$-mediated disease includes obtaining a therapeutically detectable and beneficial effect on a patient suffering from a $PrP^{Sc}$-mediated disease.

The documented competition of the anti-PrP monoclonal antibody 3F4 for the interaction between $PrP^{C}$ and $PrP^{Sc}$ provides an alternate strategy for an assay to screen for compounds able to block prion induction. In one embodiment, $PrP^{C}$ is derivatized, e.g., with Streptavidin, and immobilized to a solid support, for example, the bottom of the wells of a 96-well plate. Candidate compounds are tested for the ability to displace 3F4 from $PrP^{C}$. Binding is quantitated through standard measures, for example, by determining the amount of free antibody. Variations in this assay include use of various $PrP^{C}$-like molecules from recombinant sources.

$PrP^{Sc}$ Assay System.

In one aspect, the invention features an assay for $PrP^{Sc}$. Since $PrP^{Sc}$ binds tightly to $PrP^{C}$, the displacement of labelled PrP peptide from the prion protein complex can be used to assay for the presence of $PrP^{Sc}$. In one embodiment of this method of the invention, the displacement of labelled recombinant PrP (Hu 90–231) (SEQ ID NO:10) from the prion protein complex formed between $PrP^{C}$ and Hu 90–231 is used to assay for the presence of $PrP^{Sc}$. In the $PrP^{Sc}$ assay method of the invention, either the PrP peptide or PrP component may be labelled. Appropriate labels are known to the art, and include radioisotopes, fluorescent dyes, or spectrophotometrically-detectable chromophores.

As described above, the formation of prion protein complexes composed of $PrP^{C}$/PrP peptide, $PrP^{C}$/recombinant PrP (90–231), or recombinant PrP (90–231)/PrP peptide require an excess of the second component which has a random coil and/or α-helical conformation. In a preferred embodiment of the $PrP^{Sc}$ assay herein described, the second component is labelled. Initial experiments used a first to second component ratio of 1:5000, and subsequent optimizing experiments reduced the ratio to 1:500. Once the prion protein complex is formed, excess second component is easily removed by ultracentrifugation since the prion protein complexes are insoluble. The stoichiometry of the complexes has been determined to be approximately 1:1.

The amount of displaced PrP peptide is measured after the addition of $PrP^{Sc}$. Since $PrP^{C}$/$PrP^{Sc}$ complexes are insoluble, the displaced peptide molecules are measured in the supernatant fraction after ultracentrifugation. In another embodiment, $PrP^{C}$ is affinity labelled and bound to a solid phase after complex formation. When $PrP^{Sc}$ binds to the $PrP^{C}$ immobilized by attachment to the solid phase, the amount of displaced labelled peptides is measured in the unbound phase. Thus, the assay is calibrated by addition of known amounts of $PrP^{Sc}$, and the amount of $PrP^{Sc}$ present in an unknown sample may be determined by the amount of displaced PrP peptide.

Immobilization of $PrP^{C}$ or recombinant PrP can be accomplished by methods known to the art, e.g., chemical modification using activated biotin. The biotinylated $PrP^{C}$ or recombinant PrP, which has been complexed by another PrP molecule such as, for example, radiolabelled SHa 90–145, is then bound to a solid phase support coated with Strepavidin (Wood & Warnke (1981) J. Histochem, Cytochem. 29:1196–1204). The addition of $PrP^{Sc}$ will displace the labelled synthetic peptide, and the amount of displaced peptide will be proportional to the amount of $PrP^{Sc}$ added. Thus, measuring the amount of soluble, unbound labelled peptide provides a sensitive, rapid, and quantitative assay for $PrP^{Sc}$.

The $PrP^{Sc}$ assay of the invention provides advantages over available immunoassays in that, for example, $PrP^{Sc}$ does not need to be soluble and $PrP^{C}$ does not need to be removed prior to detection of $PrP^{Sc}$, as required by immunodetection assays. $PrP^{Sc}$ is highly insoluble and to date, only liposomes have been found to solubilize $PrP^{Sc}$ (Gabizon et al. (1987) supra). Thus, the $PrP^{Sc}$ assay of the present invention effectively circumvents the solubility problem presented by $PrP^{Sc}$. The assay may be optimized for detection of $PrP^{Sc}$ contained in human, bovine, ovine, or porcine prions.

Design of transgenes for bioassays of prions in mice.

The above described $PrP^{Sc}$ assay may also be used in designing transgenes for more rapid and sensitive bioassays for prions.

The central region of PrP delimited by codons 96–169 appears to be the region where $PrP^{C}$ and $PrP^{Sc}$ interact when a complex between the two molecules is formed (Telling et al. (1995) Cell 83:79–90). The prion protein complexes formed between $PrP^{C}$/PrP peptide, $PrP^{C}$/recombinant PrP, or recombinant PrP/PrP peptide can be used to define interactions between $PrP^{C}$ and $PrP^{Sc}$ which are more sensitive than the naturally occurring one studied to date. Changing the sequence of the first component of the complex may identify residues which permit tighter bonding of the non-homologous second component. Once such sequences are defined, the transgenic expressing such modified $PrP^{C}$ molecules may be inoculated with prions and the incubation times measured.

In one embodiment, intermediate screening may be used employing the yeast two hybrid system. The study of interacting PrP molecules can be rapidly performed with the yeast two hybrid system, e.g., one of the PrP genes is mutagenized and screened for increased interactions, as described by Chien et al. (1991) Proc. Natl. Acad. Sci. USA 88:9578–9582. Once such clones are identified, synthetic peptides or recombinant PrP molecules are produced and evaluated for prion protein complex formation. When prion protein complexes are avidly formed, transgenes with those sequences are constructed for micro-injection to produce transgenic mice by methods known in the art.

The affinity of the second component for the first is assessed by the concentration of the second component required to form prion protein complexes. Once sequences are identified that lower the concentration of the second component required for prion protein complex formation, the affinity of the second component for the first component is measured by, for example, surface plasmon resonance (Fagerstam et al. (1990) J. Mol. Recognit. 3:208–214; Stenberg et al. (1991) J. Colloid Interface Sci. 143:513–526; Liedberg & Lundstrom (1993) Sensors Actuators B 11:63–72). The first component is immobilized on a gold film and the second component is then bound. The binding of the second component is detectable as a change in the refractive index.

The method of the invention is optimized for transgenes for bioassay of human, bovine, ovine, and porcine prions. This approach has important implications for construction of a universal transgene for bioassay of human prions. As recently described in work from this laboratory, amino acid mismatches at residues 102 and 129, but not 200, result in substantial prolongation of the incubation time required for onset of PrP-mediated disease (Telling et al. (1995) supra). Identifying amino acid side chains at these and other critical residues that will permit transmission of all human prions without regard to the amino acid sequence of $PrP^{Sc}$ may be accomplished with the above described assay methodology. In addition to developing a universal transgene with respect to the sequence of $PrP^{Sc}$, the above described approach may be utilized to create an artificial $PrP^C$ which interacts with human $PrP^{Sc}$ more efficiently than naturally occurring human $PrP^C$ itself. Thus, a more sensitive and rapid bioassay for human prions may be developed with the use of the invention.

EXAMPLES

The following examples are put forth so as to provide those of ordinary skill in the art with a complete disclosure and description of how to make and use the assays of the invention, and are not intended to limit the scope of what the inventors regard as their invention. Efforts have been made to ensure accuracy with respect to numbers used (e.g., amounts, temperatures, etc.) but some experimental error and deviations should be accounted for. Unless otherwise indicated, temperature is in degrees Centigrade, molecular weight is average molecular weight, and pressure is at or near atmospheric.

Example 1

Materials and Methods

SHaPrP was subcloned into the glutamine synthetase expression vector, pEE 12 (Cell/Tech, Alameda, Calif.). Chinese hamster ovary (CHO)K1 cells (ATCC) were seeded at $10^6$ cells per 10 cm dish in GMEM-S medium containing 10% dialyzed fetal calf serum (FCS)(Gibco-BRL) (Bebbington & Hentschel (1987) in: DNA Cloning: A Practical Approach (Glover, D. M., ed.); IRL Press, Oxford, pp. 163–188). Cells were transfected with 10 μg of pEE 12-SHaPrP vector per dish using the $CaPO_4$ method (Gorman (1985) in DNA Cloning: A Practical Approach supra, pp. 143–190). After growing cells in 25 μM methionine sulfoximine (MSX)(Sigma) for 2 weeks, 60 clones were randomly selected, and grown in 100, 200, or 400 μM MSX. The clones were analyzed by Western blot to identify the highest expressors (Towbin et al. (1979) Proc. Natl. Acad. Sci. USA 76:4350–4354). From clone #30C1, phosphatidylinositol-specific phospholipase C (PIPLC) digestion released ~90 ng $SHaPrP^C$ from $10^6$ cells (Koke et al. (1991) Protein Expr. Purif. 2:51–58).

A recombinant PrP of 142 amino acids corresponding to Syrian hamster (SHa) PrP residues 90–231 (SEQ ID NO:2) was expressed at high levels in *E. coli* and purified to homogeneity under renaturing conditions.

The CHO cells expressing $SHaPrP^C$ were metabolically radiolabeled with [$^{35}$S-]Met (100 μCi/ml, NEN)(Borchelt et al. (1990) J. Cell Biol. 110:743–752), and immunoaffinity purified (Pan et al. (1992) Protein Sci. 1:1343–1352) from lysates using the anti-PrP 3F4 monoclonal antibody (mAb) (Kascsak et al. (1987) J. Virol. 61:3688–3693) which recognizes SHaPrP residues 109–112 (Rogers et al. (1991) J. Immunol. 147:3568–3574). $SHaPrP^C$ was eluted from mAb/protein A Sepharose with 3M guanidine hydrochloride (Gdn-HC1), centrifuged at 16,000×g for 2 min at 4° C., and the supernatant diluted 1:10 in TN buffer (130 mM NaCl, 10 mM Tris-HCl, pH 7.4); in some cases, $PrP^C$ was precipitated with 4 volumes of methanol to separate it from the Gdn-HCl and residual detergent. [$^{35}$S-]$PrP^C$ concentrations were determined by comparison with signals from Western blots with known quantities of $PrP^C$ from SHa brain, and by measurements in a scintillation spectrometer.

Syrian hamsters (Lak:LVG) obtained from Charles River Laboratories were inoculated with Sc237 prions (Marsh & Kimberlin (1975) J. Infect. Dis. 131:104–110) and sacrificed when they showed signs of CNS dysfunction. $SHaPrP^{Sc}$ was purified from the brains of these ill animals according to the method of Turk et al. (1988) Eur. J. Biochem. 176:21–30, herein specifically incorporated by reference). Similarly, mouse (Mo) $PrP^{Sc}$ was purified from the brains of ill mice inoculated with RML prions (Chandler (1961) Lancet 1:1378–1379). $SHaPrP^C$ was purified from the brains of uninoculated adult SHa (Pan et al. (1993) Proc. Natl. Acad. Sci. USA 90:10962–10966, herein specifically incorporated by reference) and radioiodinated with [$^{1251}$] (1 mCi/50 μg $PrP^C$, Amersham) using Iodo-Beads (Pierce) according to the method of Lee & Griffiths (1984) J. Immunol. Methods 74:181–189, herein specifically incorporated by reference).

PrP peptides were synthesized and purified as described (Gasset et al. (1992) supra; Nguyen et al. (1995) supra); conformations were established by FTIR spectroscopy and CD, as described previously (Nguyen et al. (1995) Biochemistry 34:4186–4192 and Zhang et al. (1995) J. Mol. Biol. 250:514–526, both of which references are herein specifically incorporated by reference). The PrP peptides used in the experiment are identified in Table 1. The PrP peptides were synthesized from N-Fmoc-protected amino acids using either an Applied Biosystems (Foster City, Calif.) Model 430 automated synthesizer or a Millipore (Bedford, Mass.) Model 9050 Plus PepSynthesizer and purified by RP-HPLC, as described in Nguyen et al. (1995) supra.

FTIR measurements were made by transmission spectroscopy using a Perkin Elmer (Norwalk, CT) System 2000 spectrometer equipped with a microscope attachment and purged with dry nitrogen. CD spectra were recorded on a Jasco Model 720 spectropolarimeter using 0.01 cm path length cylindrical quartz cells at room temperature. Peptide concentrations are as described in Nguyen et al. (1995) supra. Proteinase K (Gibco-BRL) was used at a concentration of 50 μg/ml and incubated for 1 h at 37° C. Although $PrP^C$ was digested in 3M Gdn-HCl, the activity of proteinase K was reduced ~90% as measured by a colorimetric assay with carbobenzoxy-valyl-glycyl-arginine-p-nitroanilide (Boerhinger Mannheim). Digestions with proteinase K were terminated by addition of 1 mM (4-amidinophenyl) methanesulfonyl fluoride (PMSF) (Boerhinger Mannheim). SDS-PAGE was performed according to Laemmli (Laemmli (1970) Nature 227:680–685), and autoradiograms obtained. Immunoblots were formed using the ECL system (Amersham) with anti-PrP 3F4 mAb. Using a JEOL 100CX electron microscope, samples were viewed at 80 Kev after negative staining.

50 ng of [$^{35}$S-]SHaPr$P^C$ at a concentration of ~10 μg/ml were incubated in Eppendorf microfuge tubes with TN buffer for up to 48 h at 37° C. PrP peptides were mixed with immunopurified, radiolabeled $PrP^C$ in 0.3M Gdn-HCl at molar ratios ranging from 50:1 to 5000:1. Anti-PrP 3F4 mAb and 13A5 mAb (Barry & Prusiner (1986) supra) were added to SHaPr$P^C$ in molar ratios ranging from 1:1 to 50:1. 3F4 and 13A5 are mouse monoclonal antibodies which recognize amino acid residues 109–112 and 138–141, respectively, of the SHa PrP proteins (Rogers et al. (1991) J. Immunol. 147:33568–3574, herein specifically incorporated by reference). The $PrP^{Sc}$(~1 mg/ml) was pretreated with Gdn-HCl at concentrations ranging from 0 to 6M for 16 h at 37° C. Upon termination of the incubation, an equal volume of TN buffer was added to all samples and analysis performed immediately.

Example 2

Promotion of Formation of Protease-Resistant PrP by PrP Peptides.

[$^{35}$S-]SHaPr$P^C$ was incubated with a synthetic peptide or $PrP^{Sc}$. The synthetic peptides were as follows: random coil SHa 90–145 at peptide to pcpC ratios of 50:1, 500:1, or 5000:1; β-sheet SHa 90–145 at ratios of 50:1, 500:1, or 5000:1; random coil Mo 90–145 at a ratio of 5000:1; β-sheet Mo 90–145 at a ratio of 5000:1; β-sheet SHa 109–122 (H1) at a ratio of 5000:1; random coil SHa 104–122 (104H1) at a ratio of 5000:1; random coil SHa 109–141; random coil SHa 90–145(A117V) at a ratio of 5000:1. In some experiments, *E. coli* expressed SHa 90–231 was used in place of $PrP^C$. SHa 90–231 was mixed with the synthetic peptide SHa 90–145 under the same conditions described above. Incubations were performed as described in Example 1, in TN buffer containing 0.3M Gdn-HCl for 48 h at 37° C. Samples were digested with proteinase K for 1 h at 37° C., followed by SDS-PAGE and autoradiography. SDS-PAGE included undigested $PrP^C$ and SHaPr$P^{Sc}$.

Results.

Random coil SHa 90–145 incubated at a ratio of 5000:1 induced protease resistance, while SHa 90–145 in the β-sheet form did not. Mo 90–145 in either the random coil or β-sheet form did not induce protease resistance when incubated with SHaPr$P^C$. Neither Hi (containing residues 109–122) nor a longer version composed of residues 104–122 (104H1) induced protease resistance in $PrP^C$. SHa 109–141 and SHa 90–145 both induced protease resistance. The most efficient formation of protease-resistance radiolabeled $PrP^C$ was seen with the SHa 90–145(A117V) peptide in which alanine is replaced with alanine at position 117. Compared with the wild-type peptide, only 30–40% of the mutant peptide was needed to produce equivalent amounts of protease-resistant $PrP^C$. The addition of detergent (2% (w/v) Sarkosyl) disrupted the $PrP^C$/PrP peptide complexes and rendered the $PrP^C$ sensitive to protease activity. With SHa 90–145(A117V), about 30% of the [$^{35}$S-]$PrP^C$/PrP peptide complex exhibited protease resistance; with SHa 90–145, only 10–15% was resistant.

When SHa 90–145 was mixed with SHa 90–231, a complex formed which was insoluble and protease resistant.

Example 3

Solubility Characteristics of $PrP^C$/PrP Peptide Complexes.

SHaPr$P^C$ was incubated alone or with SHa 90–145 (All7V) in TN buffer containing 0.3M Gdn-HCl for 48 h; samples were centrifuged at 100,000×g for 1 h at 20° C., and the pellets resuspended in TN buffer. The sedimented pellet was examined by FTIR spectroscopy, CD, and electron microscopy (EM) as described in Zhang et al. (1995) supra. Specimens stained with 2% uranyl acetate or 2% ammonium molybdate.

Results

Less than 10% of the [$^{35}$S-]$PrP^C$ sedimented when SHaPr$P^C$ was incubated alone. With the addition of SHa 90–145(A117V), ~65% of the radiolabel pelleted. FTIR spectroscopy of the sedimented $PrP^C$/SHa 90–145 complex showed a substantial increase in β-sheet content compared to pelleted $PrP^C$. As measured by CD, the supernatant containing primarily unbound SHa 90–145 peptide remained in random coil form, as did the peptide incubated alone in TN buffer for 48 h.

When examined by electron microscopy, $PrP^C$ pellets incubated alone showed many spherical aggregates up to 20 nm in diameter. In contrast, numerous large, filamentous polymers were found in the pellets of the $PrP^C$/PrP peptide mixture.

Example 4

Anti-PrP Monoclonal Antibody Binding to $PrP^C$.

[$^{35}$S-]$PrP^C$ was incubated for 48 h with either SHa 90–145 peptide or SHaPr$P^{Sc}$ in the presence or absence of α-PrP 3F4 or 13A5 mAbs. Samples were digested with proteinase K for 1 h at 37° C. followed by SDS-PAGE and autoradiographed. SHa 90–145 was incubated with $PrP^C$ at a ratio of 5000:1 (peptide to PrP) without and with mAb 3F4 (mAb:$PrP^C$ of 50:1) or mAb 13A5 (500:1). Both 3F4 and 13A5 mAbs prevented formation of protease-resistant $PrP^C$/PrP peptide complexes.

Example 5

Spontaneous Formation of Protease-Resistant PrP.

Immunopurified $PrP^C$ (10 μg/ml) from CHO cells ([$^{35}$S] SHaPr$P^C$) transfected as described in Example 1 and $PrP^C$ (1 mg/ml) from SHa brain were incubated for 0 min, 2 min, or 48 h at 37° C. in the presence of 0.75M Gdn-HCl. Prior to digestion with proteinase K for 1 h at 37° C, samples were diluted 1:4 with TN buffer. Samples were then digested with proteinase K and analyzed by SDS-PAGE and Western blotting using the anti-PrP 3F4 mAb.

Results.

Approximately 1% of the $PrP^C$ was found to be protease resistant after 48 h under these conditions, compared to ~30% of the $PrP^C$ that was rendered resistant with the SHa 90–145(A117V) peptide. $PrP^C$ overexpressed in CHO exhibited a broad size range, presumably due to hyperglycosylation in contrast to $PrP^C$ from SHa brain. To confirm the identity of the protease-resistant band, the blot was autoradiographed; after 4 weeks exposure, faint but discrete bands of identical size were detected in lanes containing $^{35}$S-Pr$P^C$. The addition of 0.2% Sarkosyl rendered the "protease-resistant" $PrP^C$ sensitive to proteolytic digestion.

Example 6

Effect of $PrP^{Sc}$ Denaturation With Gdn-HCl.

$SHaPrP^{Sc}$ was incubated with 0, 3M, or 6M Gdn-HCl for 0 min, 2 min, or 48 h at 37° C. followed by digestion with proteinase K for 1 h. Samples were analyzed by SDS-PAGE and Western blotting using the anti-PrP 3F4 mAb.

Results.

When $PrP^{Sc}$ (denatured in 3M Gdn-HCl, then diluted in buffer to a final concentration of 0.3–2M Gdn-HCl) was mixed with $PrP^{C}$, no protease-resistant [$^{35}$S-]$PrP^{C}$ was produced. However, as shown in Example 2, mixing undenatured $PrP^{Sc}$ with $PrP^{C}$ did produce protease-resistant [$^{35}$S-]$PrP^{C}$. A 10-fold excess of $PrP^{Sc}$ was insufficient to produce protease-resistant [35S-]$PrP^{C}$; a 50-fold excess of $PrP^{Sc}$ was required. The presence of 0.3M Gdn-HCl in the reaction mixture seemed to be essential since its removal by methanol precipitation prior to mixing prevented complex formation. About 50% of the [$^{35}$S-]$PrP^{C}$ was recovered in complexes sedimented at 100,000×g for 1 h, of which 10–15% were protease resistant.

Example 7

Anti-PrP Monoclonal Antibody Prevents Binding of $PrP^{Sc}$ to $PrP^{C}$.

[$^{35}$S-] $PrP^{C}$ was incubated for 48 h with either SHa 90–145 peptide or $SHaPrP^{Sc}$ in the presence or absence of anti-PrP 3F4 or 13A5 in a mAb/$PrP^{C}$ ratio of 500:1, and the formation of a $PrP^{C}$/$PrP^{Sc}$ complex determined as described above. The interaction between $PrP^{C}$ and $PrP^{Sc}$ was found to be inhibited by the anti-PrP mAb 3F4, but not 13A5.

A $PrP^{C}$ peptide truncated at the N-terminus and lacking the 3F4 epitope, $PrP^{C}$-II, was incubated with $PrP^{Sc}$, and the formation of protease resistance determined. $PrP^{C}$-II did not exhibit protease resistance.

Example 8

Effect of Detergent on $SHaPrP^{C}$ Incubated with MoPrPSC or $SHaPrP^{Sc}$.

[$^{35}$S-]$SHaPrP^{C}$ was incubated for 48 h with unlabeled $MoPrP^{Sc}$ or $SHaPrP^{Sc}$ in the absence or presence of 0.2%, 1%, or 2% Sarkosyl. Samples were analyzed by SDS-PAGE and Western blotting using the anti-PrP 3F4.

Results. When $MoPrP^{Sc}$ was mixed with $SHaPrP^{C}$, relatively little protease-resistant $PrP^{C}$ was formed, and the addition of Sarkosyl rendered the complex sensitive to proteolysis. In contrast, the [$^{35}$S-]$PrP^{C}$/$SHaPrP^{Sc}$ complex was resistant to proteolysis, even when exposed with up to 2% Sarkosyl for 48 h prior to digestion.

We claim:

1. A method of screening for compounds which inhibits the binding of $PrP^C$ to a PrP peptide, comprising the steps of:

(a) contacting in vitro a test compound with a purified naturally occurring first component $PrP^C$ in the presence of a purified second component PrP peptide, wherein said PrP peptide has a random coil or α helical confirmation, and wherein the first and second components form a prion protein complex with a $PrP^{SC}$ characteristic selected from the group consisting of (1) increased β-sheet content, (2) diminished aqueous solubility, and (3) resistance to poroteolytic digestion, relative to $PrP^C$;

(b) detecting formation of a prion protein complex; by determining (1) increased β-sheet, (2) diminished aqueous solubility, or (3) resistance to proteolytic digestion, relative to PrPc and and (c) comparing levels of prion protein complex in the presence of said test compound with levels in the absence of the test compound, wherein reduced levels of said prion protein complex in the presence of said test compound is indicative that said test compound inhibits said binding of $PrP^C$ to a PrP peptide.

2. The method of claim 1, wherein the prion protein complex has increased insolubility relative to $PrP^C$.

3. The method of claim 2, wherein said complex has increased β-sheet conformation relative to the first component $PrP^C$.

4. The method of claim 1, wherein said first component $PrP^C$ is selected from the group consisting of human $PrP^C$, hamster $PrP^C$, mouse $PrP^C$, bovine $PrP^C$, and ovine $PrP^C$.

5. The method of claim 4, wherein said $PrP^C$ is human $PrP^C$.

6. The method of claim 1, wherein said first component $PrP^C$ is the peptide having the amino acid sequence of SEQ ID NO:10.

7. The method of claim 2, wherein said second component is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NQ:8, SEQ ID NO:9, and SEQ ID NO:10.

8. A method for screening compounds which inhibit induction of a prion protein complex, comprising the steps of:

(a) contacting in vitro a test compound with a purified naturally occurring first component $PrP^C$ in the presence of a second purified component PrP peptide wherein said PrP peptide has a random coil or α helical confirmation, and wherein the first and second components form a prion protein complex with a $PrP^{SC}$ characteristic selected from the group consisting of (1) increased β-sheet context, (2) diminished aqueous solubility, and (3) resistance to poroteolytic digestion, relative to $PrP^C$;

(b) detecting induction of the prion protein complex; by determining (1) increased β-sheet content, (2) diminished aqueous solubility, or (3) resistance to proteolytic digestion, relative to PrPc and (c) comparing induction of the prion protein complex in the presence of said test compound with induction of the protein prion complex in the absence of the test compound, wherein reduced levels of said prion protein complex in the presence of said test compound is indicative that said test compound inhibits induction.

9. The method of claim 8, wherein said prion protein complex has increased insolubility relative to $PrP^C$.

10. The method of claim 8, wherein said first component $PrP^C$ is selected from the group consisting of human $PrP^C$, hamster $PrP^C$, mouse $PrP^C$, bovine $PrP^C$, and ovine $PrP^C$.

11. The method of claim 10, wherein said $PrP^C$ is human $PrP^C$.

12. A method for screening compounds which inhibit induction of a prion protein complex, comprising the steps of:

(a) contacting in vitro a test compound with a first component PrPc having, the amino acid sequence of SEQ ID NO: 10 in the presence of a second purified component PrP peptide wherein said PrP peptide has a random coil or α helical confirmation and wherein the first and second components form a prion protein complex with a PrPsc characteristic selected from the group consisting of (1) increased β-sheet content, (2) diminished aqueous solubility and (3) resistance to proteolytic digestion, relative to PrPc;

(b) detecting induction of the prion protein complex by determining (1) increased β-sheet content, (2) diminished aqueous solubility or (3) resistance to proteolytic digestion, relative to PrPc; and (c) comparing induction of the prion protein complex in the presence of said test compound with induction of the protein prion complex in the absence of the test compound, wherein reduced levels of said prion protein complex in the presence of said test compound is indicative that said test compound inhibits induction.

13. The method of claim 8, wherein said second component is selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

14. An assay methodology, comprising:

providing a purified naturally occurring $PrP^C$ protein;

contacting the $PrP^C$ protein with a test compound;

combining a purified peptide with the $PrP^C$ protein which peptide is characterized by having a random coil or α helical confirmation and causing the $PrP^C$ protein to undergo conformational changes including the formation of β-sheets in the absence of the test compound; and determining the effect of the test compound on preventing the conformational changes.

15. The assay methodology of claim 14, wherein conformational changes result in increased insolubility as compared to $PrP^C$.

16. The assay methodology of claim 14, wherein conformational changes result in increased protease resistance as compared to $PrP^C$.

17. The assay methodology of claim 14, wherein $PrP^C$ is selected from the group consisting of human $PrP^C$, hamster $PrP^C$, mouse $PrP^C$, bovine $PrP^C$, and ovine $PrP^C$.

18. The assay methodology of claim 17, wherein $PrP^C$ is human $PrP^C$.

19. The assay methodology of claim 14, wherein $PrP^C$ is a human naturally occurring variant of $PrP^C$.

20. An assay for $PrP^{Sc}$, said assay comprising the steps of:

(a) mixing a first component of purified naturally occurring $PrP^C$ and a purified second component PrP peptide wherein said peptide has a random coil or α helical confirmation under conditions in which a prion protein complex is formed;

(b) adding a test sample suspected of containing $PrP^{Sc}$;

(c) measuring the amount of PrP peptide displaced from the prion protein complex by formation of $PrP^C/PrP^{Sc}$ complexes, wherein the amount of PrP peptide displaced from the prion protein complex is proportional to the amount of $PrP^{Sc}$ present in the test sample.

21. The method of claim 20, wherein the second component PrP peptide is labelled and the amount of PrP peptide displaced from the prion protein complex is measured by removing the $PrP^C/PrP^{Sc}$ complex and determining the amount of label remaining.

22. The method of claim 20, wherein the first component $PrP^C$ is immobilized by attachment to a solid phase, and the amount of displaced labelled PrP peptide is measured in the unbound phase.

23. The method of claim 21, wherein the PrP peptide is labeled with a reagent selected from the group consisting of a radioactive isotope, a fluorescent dye, and a chromophore.

24. The method of a claim 1, wherein the prion protein complex comprises a fibrous aggregate, of which at least 65% sediments at 100,000×g for 1 hour at 20° C.

25. The method of claim 1, wherein the prion protein complex is at least 20% protease resistant relative to said PrPc.

26. The method of a claim 8, wherein the prion protein complex comprises a fibrous aggregate, of which at least 65% sediments at 100,000×g for 1 hour at 20° C.

27. The method of claim 8, wherein the prion protein complex is at least 20% protease resistant relative to said PrPc.

* * * * *

UNITED STATES PATENT AND TRADEMARK OFFICE

CERTIFICATE OF CORRECTION

PATENT NO. : 5,750,361
DATED : May 12, 1998
INVENTOR(S) : Stanley B. Prusiner; Kiyotoshi Kaneko; Fred E. Cohen It is certified that error appears in the above-identified patent and that said Letters Patent is hereby corrected as shown below:

Title page,
Item [75], change inventor name "Kivotoshi Kaneko" to -- Kiyotoshi Kaneko --;

Column 26,
Lines 38 and 44, of claims 25 and 27, change "PrPc" to -- $PrP^C$ --.

Signed and Sealed this

Eleventh Day of December, 2001

*Attest:*

Nicholas P. Godici

NICHOLAS P. GODICI

*Attesting Officer* *Acting Director of the United States Patent and Trademark Office*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 56 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Gly Gln Gly Gly Gly Thr His Asn Gln Trp Asn Lys Pro Ser Lys Pro
                 5                  10                  15

Lys Thr Asn Met Lys His Met Ala Gly Ala Ala Ala Ala Gly Ala Val
            20                  25                  30

Val Gly Gly Leu Gly Gly Tyr Met Leu Gly Ser Ala Met Ser Arg Pro
        35                  40                  45

Met Met His Phe Gly Asn Asp Trp
    50                  55
```

( 2 ) INFORMATION FOR SEQ ID NO:2:

( i ) SEQUENCE CHARACTERISTICS:
( A ) LENGTH: 142 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Gly Gln Gly Gly Gly Thr His Asn Gln Trp Asn Lys Pro Ser Lys Pro
                 5                  10                  15

Lys Thr Asn Met Lys His Met Ala Gly Ala Ala Ala Ala Gly Ala Val
```

-continued 20 25 30

Val Gly Gly Leu Gly Gly Tyr Met Leu Gly Ser Ala Met Ser Arg Pro
35 40 45

Met Met His Phe Gly Asn Asp Trp Glu Asp Arg Tyr Tyr Arg Glu Asn
50 55 60

Met Asn Arg Tyr Pro Asn Gln Val Tyr Tyr Arg Pro Val Asp Gln Tyr
65 70 75 80

Asn Asn Gln Asn Asn Phe Val His Asp Cys Val Asn Ile Thr Ile Lys
85 90 95

Gln His Thr Val Thr Thr Thr Thr Lys Gly Glu Asn Phe Thr Glu Thr
100 105 110

Asp Ile Lys Ile Met Glu Arg Val Val Glu Gln Met Cys Thr Thr Gln
115 120 125

Tyr Gln Lys Glu Ser Gln Ala Tyr Tyr Asp Gly Arg Arg Ser
130 135 140

( 2 ) INFORMATION FOR SEQ ID NO:3:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( x i ) SEQUENCE DESCRIPTION: SEQ ID NO:3:

Met Lys His Met Ala Gly Ala Ala Ala Ala Gly Ala Val Val
5 10

( 2 ) INFORMATION FOR SEQ ID NO:4:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( x i ) SEQUENCE DESCRIPTION: SEQ ID NO:4:

Leu Lys His Val Ala Gly Ala Ala Ala Ala Gly Ala Val Val
5 10

( 2 ) INFORMATION FOR SEQ ID NO:5:

( i ) SEQUENCE CHARACTERISTICS:
( A ) LENGTH: 19 amino acids
( B ) TYPE: amino acid
( D ) TOPOLOGY: linear ( i i ) MOLECULE TYPE: peptide ( x i ) SEQUENCE DESCRIPTION: SEQ ID NO:5:

Lys Pro Lys Thr Asn Met Lys His Met Ala Gly Ala Ala Ala Ala Gly
5 10 16

Ala Val Val
19

( 2 ) INFORMATION FOR SEQ ID NO:6:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( x i ) SEQUENCE DESCRIPTION: SEQ ID NO:6:

Met Leu Gly Ser Ala Met Ser Arg Pro Met Met His Phe
5 10

( 2 ) INFORMATION FOR SEQ ID NO:7:

( i ) SEQUENCE CHARACTERISTICS:
( A ) LENGTH: 33 amino acids
( B ) TYPE: amino acid
( D ) TOPOLOGY: linear ( i i ) MOLECULE TYPE: peptide ( x i ) SEQUENCE DESCRIPTION: SEQ ID NO:7:

Met Lys His Met Ala Gly Ala Ala Ala Ala Gly Ala Asp Asp Gly Gly
5 10 15

Leu Gly Gly Tyr Met Leu Gly Ser Ala Met Ser Arg Pro Met Met His
20 25 30

Glu
33

( 2 ) INFORMATION FOR SEQ ID NO:8:

( i ) SEQUENCE CHARACTERISTICS:
( A ) LENGTH: 62 amino acids
( B ) TYPE: amino acid
( D ) TOPOLOGY: linear ( i i ) MOLECULE TYPE: peptide ( x i ) SEQUENCE DESCRIPTION: SEQ ID NO:8:

Gly Gln Gly Gly Gly Thr His Asn Gln Trp Asn Lys Pro Ser Lys Pro
5 10 15

Lys Thr Asn Met Lys His Met Ala Gly Ala Ala Thr Ala Gly Ala Val
20 25 30

Val Gly Gly Leu Gly Gly Tyr Met Leu Gly Ser Ala Met Ser Arg Pro
35 40 45

Met Met His Phe Gly Asn Asp Trp Gly Ala Ala Asp Ala Gly
50 55 60 62

( 2 ) INFORMATION FOR SEQ ID NO:9:

( i ) SEQUENCE CHARACTERISTICS:
( A ) LENGTH: 56 amino acids
( B ) TYPE: amino acid
( D ) TOPOLOGY: linear ( i i ) MOLECULE TYPE: peptide ( x i ) SEQUENCE DESCRIPTION: SEQ ID NO:9:

Gly Gln Gly Gly Gly Thr His Asn Gln Trp Asn Lys Pro Ser Lys Pro
5 10 15

Lys Thr Asn Leu Lys His Tyr Ala Gly Ala Ala Ala Ala Gly Ala Val
20 25 30

Val Gly Gly Leu Gly Gly Tyr Met Leu Gly Ser Ala Met Ser Arg Pro
35 40 45

Met Ile His Phe Gly Asn Asp Trp
50 55

( 2 ) INFORMATION FOR SEQ ID NO:10:

( i ) SEQUENCE CHARACTERISTICS:
( A ) LENGTH: 142 amino acids

-continued ( B ) TYPE: amino acid
( D ) TOPOLOGY: linear ( i i ) MOLECULE TYPE: peptide ( x i ) SEQUENCE DESCRIPTION: SEQ ID NO:10:

```
Gly Gln Gly Gly Gly Thr His Ser Gln Trp Asn Lys Pro Ser Lys Pro
                5                   10                  15

Lys Thr Asn Met Lys His Met Ala Gly Ala Ala Ala Ala Gly Ala Val
            20                  25                  30

Val Gly Gly Leu Gly Gly Tyr Met Leu Gly Ser Ala Met Ser Arg Pro
        35                  40                  45

Ile Ile His Phe Gly Ser Asp Tyr Glu Asp Arg Tyr Tyr Arg Glu Asn
    50                  55                  60

Met His Arg Tyr Pro Asn Gln Val Tyr Tyr Arg Pro Met Asp Glu Tyr
65                  70                  75                  80

Ser Asn Gln Asn Asn Phe Val His Asp Cys Val Asn Ile Thr Ile Lys
                85                  90                  95

Gln His Thr Val Thr Thr Thr Thr Lys Gly Glu Asn Phe Thr Glu Thr
            100                 105                 110

Asp Val Lys Met Met Glu Arg Val Val Glu Gln Met Cys Ile Thr Gln
        115                 120                 125

Tyr Glu Arg Glu Ser Gln Ala Tyr Tyr Gln Arg Gly Ser Ser
    130                 135                 140
```